United States Patent [19]

Kitajima et al.

[11] 4,437,970

[45] Mar. 20, 1984

[54] DEVICE FOR DETERMINING IONIC ACTIVITY

[75] Inventors: Masao Kitajima; Osamu Seshimoto; Kikuo Kubotera; Akira Yamaguchi, all of Saitama, Japan

[73] Assignee: Fuji Photo Film Co., Ltd., Kanagawa, Japan

[21] Appl. No.: 500,600

[22] Filed: Jun. 2, 1983

[30] Foreign Application Priority Data

Jun. 2, 1982 [JP] Japan .................................. 57-94575

[51] Int. Cl.³ ...................... G01N 27/46; G01N 27/58
[52] U.S. Cl. .................................. 204/412; 204/416; 204/435
[58] Field of Search ............... 204/412, 416, 435, 1 T; 422/68, 50

[56] References Cited

U.S. PATENT DOCUMENTS

| | | | |
|---|---|---|---|
| 4,053,381 | 10/1977 | Hamblen et al. | 204/416 |
| 4,171,246 | 10/1979 | Hamblen et al. | 204/1 T |
| 4,233,029 | 11/1980 | Columbus | 204/416 X |
| 4,271,119 | 6/1981 | Columbus | 204/416 X |
| 4,273,639 | 6/1981 | Gottermeier | 204/435 X |
| 4,302,313 | 11/1981 | Columbus | 204/435 X |

*Primary Examiner*—G. L. Kaplan
*Assistant Examiner*—Nam X. Nguyen
*Attorney, Agent, or Firm*—Sughrue, Mion, Zinn, Macpeak & Seas

[57] ABSTRACT

A device for determining ionic activity composed of, as essential components, plural pairs of ion-selective solid electrodes each pair having two electrodes (one electrode on each of two sides) and each pair having a different ion-selective layer; two liquid distribution porous members, each member disposed over all the electrodes of each said side of the plural pairs; and a porous capillary bridge disposed on or between the liquid distribution porous members. The bridge can be in liquid contact with all the electrodes through the liquid distribution porous members and achieve electrical conduction between two electrodes in each pair after spotting a test solution and a reference solution. The device preferably further comprises a support frame and a cover having two apertures for liquid spotting. The device can simultaneously determine ionic activities of a plurality of different ions in a test solution, such as whole blood, plasma, serum, urine, etc., by spotting a test solution and a reference solution each in one operation and measuring an electrical potential difference of each pair.

19 Claims, 7 Drawing Figures

DEVICE FOR DETERMINING IONIC ACTIVITY

FIELD OF THE INVENTION

This invention relates to a device effective for the determination of concentrations or activities of specific ions contained in a liquid or a solution. More particularly, the invention relates to a device for determining ionic activities comprising ion-selective solid electrodes (hereinafter, are sometimes referred to as solid electrodes) for potentiometrically measuring ion concentrations or ionic activities (hereinafter, they are referred to as ionic activities) of, in particular, aqueous liquids or solutions in body fluids of a living body, such as whole blood, blood plasma, serum, lymph, spinal fluid, urine, etc., said device being capable of determining ionic activities of different ions contained in a same single test liquid or test solution simultaneously or successively by one operation.

BACKGROUND OF THE INVENTION

Conventional techniques use a wide variety of devices for determining ionic activities in solutions such as dry type ion-selective electrodes. The methods using these electrodes are determined from the veiwpoints of easiness in maintenance, storage and handling at measurement as well as of low cost. For example, rod-form or probe-form ion-selective solid electrodes are disclosed in U.S. Pat. No. 4,115,209, Japanese Utility Model Publication No. 14472/65, U.S. Pat. No. 3,718,569, etc. Also, ion-selective solid electrodes each composed of a support having formed thereon a laminate structure of four-functional layers, a laminate structure of three-functional layers, or a laminate structure of two-functional layers as film-shaped structure are disclosed in, for example, *Research Disclosure*, #16113 Sept., 1977), U.S. Pat. Nos. 4,053,381, 4,115,209, 4,214,968, Japanese Patent Application (OPI) Nos. 17851/82 and 17852/82, etc. (the term "OPI" as used herein refers to a "published unexamined Japanese patent application"). Such an ion-selective electrode is generally composed of a structure comprising an electrically insulating support having laminated thereon, in succession, a metal layer, a layer of a water-insoluble salt of the metal same as the metal of the aforesaid metal layer, a dried reference electrolyte layer composed of a hydrophilic binder matrix having dissolved therein a water-soluble salt having a common anion to the water-insoluble salt layer (dried reference electrolyte layer is omitted in the foregoing three-functional laminate layer type ion-selective electrode), and an ion selective layer. Furthermore, U.S. Pat. No. 4,115,209 discloses ion-selective electrodes of a two-functional layer laminate structure wherein a conductive material is coated with an ion-selective layer containing an ion-exchange material.

Devices for determining ionic activity using such ion-selective electrodes include a device composed of a pair of juxtaposed ion-selective electrodes and a capillary bridge (hereinafter, is simply referred to as bridge) for attaining electric conduction between the electrodes by being formed on these electrodes to electrically connect them. A determination method using the device is performed by spotting a test solution and a reference solution onto definite positions, respectively, of the electrodes to cause an electric conduction between both solutions through the bridge and measuring the potential difference occurring between the electrodes by means of a potential measuring device. That is, the solutions spotted on the surfaces of the electrodes wet the surfaces thereof and at the same time diffuse into the bridge disposed on the electrodes by a capillary phenomenon. The solutions are brought into contact with each other at a thin contact interface, whereby an electric conduction is attained between the electrodes to make it possible to measure the potential between the electrodes. In this case, each ion-selective electrode has an ion-selective layer selectively responsive to a predetermined specific ion as the outermost layer. The ion-selective layer is a layer which is generally composed of an ion carrier, a solvent for the ion carrier, and a polymer binder. The ion-selective layer can be selectively responsive to a specific ion by selecting the ion carrier and the solvent for the ion carrier. This means that in the case of determining the ionic activity of each of $Na^+$, $K^+$, $Ca^{2+}$, $Cl^-$, etc., in, for example, serum solid electrodes, each having a different specific ion-selective layer (the layer may be an ion-permeable protective layer described below in case of determining the ionic activity of $Cl^-$) must be separately prepared.

The inventors previously proposed a device for determining ionic activity comprising plural pairs of juxtaposed solid electrodes each pair having a different ion-selective layer and a single porous bridge disposed on all the electrodes (Japanese Patent Application No. 82986/82 (corresponding to U.S. application Ser. No. 495,329, filed May 17, 1983)). One embodiment of the invention of the foregoing patent application is explained by referring to FIG. 1 and FIG. 2 of the accompanying drawings. That is, FIG. 1 is a plan view of the embodiment of the device for determining ionic activity of the foregoing patent application and FIG. 2 is a cross sectional view taken along the line I—I in FIG. 1. The device illustrated in FIG. 1 is composed of three pairs of solid electrodes 23 (23a and 23b), 24 (24a and 24b), and 25 (25a and 25b) each pair having a different ion-selective layer showing a selectivity for each specific ion and the solid electrodes having, for example, the laminated layer structures as shown in FIG. 2. The ion-selective electrodes are each composed of an electrically insulating support 1 having laminated thereon a conductive metal layer 2, a reference electrolyte layer 4 (the reference electrolyte layer may be omitted), and an ion-selective layer 5 (for the electrode pairs 23 and 24) or an ion-permeable protective layer (for the electrode pair 25). As is clear from FIG. 2, each pair of electrodes is electrically isolated from other electrodes. Furthermore, the electrodes in each pair of electrodes are also insulated from each other. Each pair of electrodes has terminals 13 for electric connection at both ends thereof, said terminals 13 being formed by exposing the metal layer (not shown) of the solid electrode at the end portions, and a potential measuring device (not shown) is brought into contact with the electrodes at the exposed portions through probes to measure a potential difference between the electrodes. The whole surface of the metal layers of the electrodes except the terminal portions 13 are covered by functional layers constituting the electrodes laminated on the metal layers. In another embodiment, in place of forming the terminal portions 13 by exposing the metal layers at the portions as described above, the whole surface of the metal layer is covered by the functional layers without exposing terminal portions and stylus probes of a potential measuring device may be brought into contact with the metal layers of the electrodes by piercing the stylus probes through the layers on the metal layers from the uppermost layer to measure the potential difference between the electrodes.

A single porous capillary bridge 19 is placed over all the solid electrodes for electrically connecting or conducting two individual electrodes in each pair of the solid electrodes. The bridge 19 has apertures 20 and 22 capable of applying each test solution and reference solution onto a definite position of the surface of each electrode in each pair. When the solutions are spotted onto these apertures, each of the solutions wets the surface of the electrode at the spotted portion and also permeates and diffuses into the bride 19 from the inside wall of the aperture. The porous layer of the bridge 19 is sealed at the edge portions 11 to prevent the solutions from being oozed from the edges of the bridge 19. The foregoing apertures have functions of enabling spotting of solutions to definite positions of the solid electrode surfaces and also as cavities for storing the solutions therein as will be understood from FIG. 2.

By spotting each of the test solutions and each of the reference solutions onto the surfaces of each pair of electrodes of the devices for determining ionic activity having the foregoing construction, the ionic activities of plural kinds of different ions each contained in each test solution can be simultaneously determined on plural items. According to the foregoing invention of our previous patent application, the determination of ionic activities can be greatly improved with respect to maintenance, storage, operation, etc.

Now, in the device for determining ionic activity provided by our previous invention described above, the function of attaining the electric conduction and the distribution of liquids, that is, the uniform distribution of test solutions and reference solutions to the surfaces of the electrodes are performed by using a sheet-form capillary bridge and hence both solutions must be spotted onto the surfaces of each pair of the electrodes in a short period of time. That is, it is necessary that the solutions spotted to the plural apertures diffuse into the bridge under the same condition to form a uniform contact interface between each pair of electrodes.

SUMMARY OF THE INVENTION

As the result of various investigations, the inventors have succeeded in attaining the present invention which can determine ionic activities of plural items in one operation since in this invention a test liquid or a test solution (hereinafter referred to as test solution) and a reference solution can be supplied to the surfaces of plural pairs of electrodes by spotting the test solution and the reference solution each only once. That is, the invention provides a device for determining ionic activity having improved operability and function, which will be further described later.

An object of this invention is to provide a device for determining ionic activity wherein by only spotting each of a test solution and a reference solution onto at least each one of independent liquid distribution porous members each disposed on plural pairs of solid electrodes, each electrode pair having one electrode on each of two sides, so that each liquid distribution porous member covering at least partially all the electrodes at each said side of the electrode pairs, the solutions are supplied to the surfaces of the plural pairs of the solid electrodes each having a different ion-selective layer, whereby ionic activities of plural items can be simultaneously or successively determined by one operation.

Another object of this invention is to provide a device for determining ionic activity capable of certainly performing the distribution and contact of solutions even if a test solution having a high viscosity, such as whole blood, etc., is used.

According to this invention, there is provided a device for determining ionic activity composed of plural pairs of ion-selective solid electrodes each pair having an ion-selective layer selectively responsive to a predetermined specific ion as the outermost layer of the solid electrode and a porous capillary bridge for achieving, after supplying a test solution and a reference solution to said pairs of solid electrodes, the electric conduction of both solutions by the permeation of the solutions through the porous capillary bridge, wherein said device comprising plural pairs of solid electrodes, each electrode pair having one electrode on each of two sides and having a different ion-selective layer, at least one porous capillary bridge having the function as above described, and at least one liquid-distribution porous member provided for each side of plural pairs of solid electrodes so that the member covers at least partially all the electrodes at each side.

DETAILED DESCRIPTION OF THE INVENTION

In the foregoing previously proposed device for determining ionic activities on plural items using plural pairs of solid electrodes and a single bridge formed thereon, both functions of the distribution of solutions (a test solution and a reference solution) and of the formation of liquid bridging or connection for achieving electric conduction of both solutions (the test solution and the reference solution) are attained using one common porous material showing capillary phenomenon. However, with the present invention the function for the distribution of solutions is structurally separated from the function of a porous material for forming a bridge. By separating the function for liquid distribution from the function of bridge in this invention, it becomes possible to simultaneously measure the activities of specific ionic components contained in a test solution having various problems, e.g., difficulty in distribution, etc., such as whole blood certainly by an easy operation. Also, by this invention, it has now become possible to measure the electric potential differences of plural pairs of ion-selective electrodes by only one spotting operation for each of a test solution and a reference solution.

The invention will now be further explained in more detail by referring to the accompanying drawings.

Figure 1:
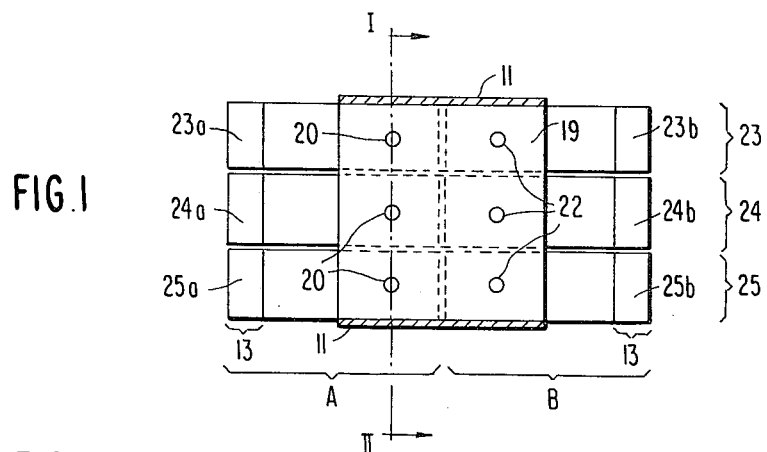
FIG. 1 is a plan view showing a device for determining ionic activity capable of determining ions of plural items previously proposed by the inventors.
Figure 2:
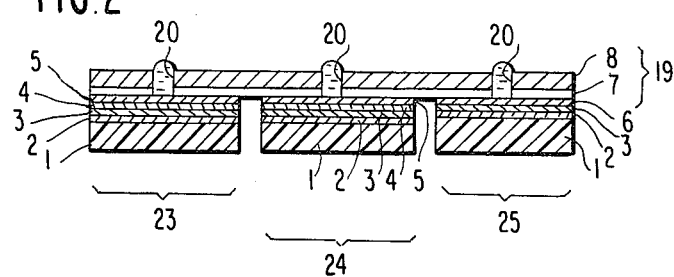
FIG. 2 is a cross sectional view taken along the line I—I in FIG. 1.
Figure 3:
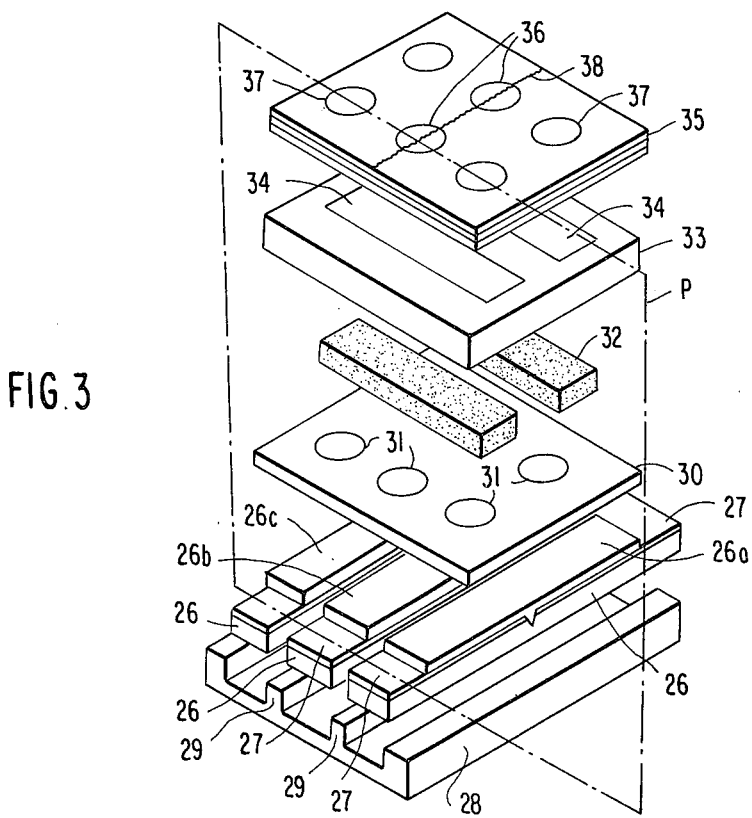
FIG. 3 is a schematic side view showing an embodiment of this invention.

FIG. 3 is a schematic side view showing an embodiment of the device for determining ionic activity of this invention. In FIG. 3 numeral 26 indicates film-shaped ion-selective solid electrodes designed in pair structure (a single electrode element comprising paired ion-selective electrodes), each pair having an ion-selective layer 26a as an outermost layer (the detailed layer structure of the solid electrodes is not shown in the figure) and each solid electrode pair 26 has terminal portions 27 for electrical connection at both end portions thereof. The plural pairs of solid electrodes 26 (each electrode pair having an each different ion-selective layer 26a, 26b or 26c) are placed in a support frame 28 having partitions 29 for electrically insulating each pair of solid electrodes from the other electrode pairs fixed thereto. A water-impermeable material layer 30 is stuck to the surface of the foregoing solid electrodes 26 so that the layer 30 uniformly covers the surfaces of all the solid electrodes 26, said layer 30 having liquid supplying apertures 31 capable of supplying the solution to definite portions of each solid electrode in each pair 26 and retaining therein the solution. Two liquid distribution porous members 32, which are the characteristic members in this invention, each connecting the domains corresponding to the electrodes 26 on one side having different ion-selective layers 26a, 26b and 26c with each other are disposed between the foregoing plural pairs of solid electrodes. A porous bridge, which has a liquid connection at each side to all electrodes in one side of pairs of electrodes through the liquid distribution porous member upon spotting of a test solution or a reference solution, is provided on or between the above described two liquid distribution members. The porous bridge will be described hereinafter. A liquid storage member or frame 33 having two liquid storage cells 34 for containing the foregoing liquid distribution porous members for storing a test solution and a reference solution, respectively, each cell for each electrode side of the foregoing plural pairs of solid electrodes, is disposed on the water-impermeable material layer on the plural pairs of solid electrodes to make the device rigid and unbendable together with the foregoing support frame 28. Also, the form of the liquid storage cell 34 is not limited to the square form as shown in FIG. 3 but any form which can connect the liquid supplying apertures 31 with each other and does not disturb the distribution of the liquids supplied to the apertures 31 may be employed in this invention.

In one embodiment of the device for determining ionic activity of this invention, a porous capillary bridge 38 is formed on and in a body with the device for connecting a test solution spotted onto one of the foregoing liquid distribution porous members 32 or liquid storage cells 34 with a reference solution spotted onto another liquid distribution porous member 32 or liquid storage cells 34 by the diffusion of both solutions to achieve an electrical conduction between both electrodes in each pair through both solutions. In another embodiment of the device for determining ionic activity of the invention, after spotting a test solution and a reference solution onto the foregoing two liquid distribution porous members 32 or liquid storage cells 34, respectively, a porous bridge 38 is brought into contact with or close to the device for achieving the electrical conduction between both electrodes in each pair through both solutions.

Figure 4:
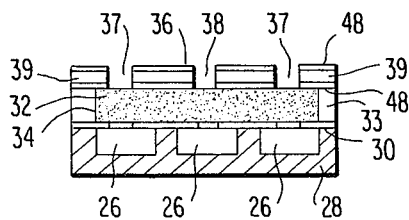
FIG. 4 is a cross sectional view taken along the plan P of the embodiment of this invention shown in FIG. 3 after assembling the whole parts.

In a preferred embodiment of this invention, a cover 35 is formed on the foregoing liquid storage member 33. That is, the cover 35 is formed on the liquid storage member 33, having a set of two apertures for liquid spotting 36 capable of supplying a test solution and a reference solution to the foregoing two liquid distribution porous members 32, respectively, in the liquid storage cells 34, and plural ventilation apertures 37. The cover 35 is shaped so that it covers the whole upper surface of the member 33. In this case, it is preferred that these apertures for liquid spotting 36 and ventilation apertures 37 be positioned as aligned with the positions of the liquid supplying apertures 31 disposed under the cover 35. Onto the upper surface of the cover 35 can be stuck the foregoing porous capillary bridge 38 composed of a twisted thread or fibers of an organic synthetic polymer at both ends of the bridge. The porosity of said bridge is plugged at both ends thereof by heat seal or by the use of an adhesive, for connecting the foregoing set of apertures for liquid spotting 36. A practical example of the device of this invention is illustrated in FIG. 4 as a sectional view although the dimensional ratio or relation of the parts shown in the figure is only for reference.

In a practical embodiment of the device of this invention, it is preferred that each film-shaped electrode be a single electrode element comprising paired ion-selective electrodes formed on a common support. Practical examples of such an electrode are described in Japanese Patent Application No. 40398/82. That is, each pair of solid electrodes is a single electrode element comprising paired ion-selective solid electrodes composed of an electrically insulating support having formed thereon, in succession, a conductive metal layer which is skived with a groove at the center by which the metal layer is divided into two electrically isolated portions, a layer of a water-insoluble salt of the metal of the aforesaid conductive metal layer, which is also divided into two portions by the groove together with the conductive metal layer, and a common ion-selective layer. The single electrode element as described above is desirable because the distance between electrodes can be greatly reduced as compared to a pair of electrodes composed of two independently disposed electrodes in a conventional device for determining ionic activity. It is also possible to greatly reduce the distance for distributing a test solution and a reference solution, the length of a bridge between a pair of electrodes, and the amount of both solutions which must be distributed.

Figure 5:
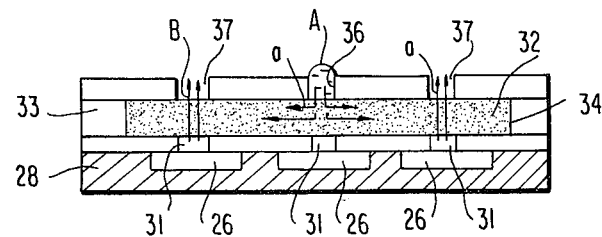
FIG. 5 is an enlarged side sectional view showing the state of determination by an embodiment of this invention.

When measuring ionic activities using the device for determining ionic activity of the present invention having the foregoing structure, for example, 50 to 60 $\mu l$ of whole blood and the same amount of a reference solution are spotted onto a set of apertures for liquid spotting 36, respectively, formed on a cover 35. As shown in FIG. 5 as an enlarged view of an embodiment of this invention, a spotted solution A is quickly absorbed by a liquid distribution porous member 32 contained in a liquid storage cell 34 of the liquid storage member 33 to be stored in the liquid storage cell and at the same time is transported by diffusion as shown by arrow a. The liquid distribution porous member 32 retains therein the solution in an amount larger than the liquid-retaining capacity thereof and thus distributes the solution onto the surface of the electrode 26. It is preferred that the liquid distribution porous member 32 be composed of a loose porous material. If a dense porous material is employed, the liquid spotted thereon forms a liquid film on the liquid supplying apertures 31 and hence the liquid is reluctant to enter the liquid supplying apertures 31.

If air exists in the inside of the liquid supplying apertures 31, the air prevents the permeation of the liquid into the liquid supplying apertures. In order to remove the air, plural ventilation apertures 37 are formed in the cover 35 covering the liquid storage cells 34 and the air is removed as shown by arrow B. Each solution thus stored in each liquid storage cell 34 is distributed to each electrode by each liquid distribution porous member 32. On the other hand, the solution A diffuses into a bridge (not shown in FIG. 5) connecting the apertures for liquid spotting 36 and is brought into contact with another solution diffused from another side of the bridge to provide an electrical conduction between electrodes in each pair, whereby a potential difference is formed between each pair of electrodes. A potential measuring device (not shown) is connected to the terminal 27 (as shown in FIG. 3) which electrically connects each pair of electrodes and thus the ionic activities of different ions are simultaneously or successively determined by one operation. In addition, the amount of the solution supplied to each electrode through each liquid supplying aperture is in the range of 10 $\mu l$ to 20 $\mu l$.

The invention will now be further explained by the following embodiments. However, the scope of the invention is not limited to these embodiments.

Solid electrodes used in the present invention can be prepared by conventionally known methods as will be described hereinafter. The support frame 28 may be prepared by a material the same as materials for an insulating support for a solid ion-selective electrode, which has an electrical insulating property, has a hardness to some extent, and can be easily processed. For example, the support frame may be composed of a sheet of a polymer such as cellulose acetate, polyethylene terephthalate, polycarbonate of bisphenol A, polystyrene, etc., a glass plate, a ceramic plate, or a paper, etc. The water-impermeable material layer 30 is, for example, composed of a double sided adhesive film or tape, to which are stuck the electrodes 26 and the liquid storage member 33. Alternatively, the water-impermeable material layer 30 and the liquid storage member 33 can be stuck using an adhesive or double sided adhesive film. The liquid distribution porous member 32 is composed of a void-having textile woven or knitted using a yarn of hydrophilic natural fibers or organic polymer fibers having at least hydrophilic surfaces, said textile being porous and easily ventilating air to transport a liquid. For example, bandage cloths, gauzes, tricot, cluster of synthetic polymer fibers, mosquito net cloths of hemp, victoria lawns or cheesecloth, cluster of glass fibers subjected to a hydrophilic treatment, asbestos, are preferably used as such materials.

The material used for the liquid distribution porous members may be treated with a surface active agent. Preferred surface active agents include nonionic surface active agents. Preferred treatment methods with the surface active agents include a method of immersing the liquid distribution member in an aqueous solution of the surface active agent followed by drying and a method of spraying an aqueous solution of the surface active agent onto the liquid distribution member followed by drying.

The liquid storage member 33 is composed of a polymer which is the same as the polymer used for the insulating support as described above, such as polystyrene, having relatively large punched apertures or rectangular holes for forming the liquid storage cells 34. The liquid storage member or upper cover can be rendered opaque by the incorporation of a fine titanium oxide powder, etc. The upper cover 35 can be omitted, and in such an embodiment, the liquid storage member is an outermost member of the device.

The cover 35 has a three-layer structure (as shown in FIG. 4) composed of a layer 39 of a polymer which is the same as the foregoing polymer used for the insulating support, such as polyethylene terephthalate film, and double sided adhesive film 48 stuck to both surfaces of the polymer layer 39. The cover 35 also has a set of apertures for liquid spotting 36 and plural ventilation apertures 37. The apertures for liquid spotting 36 and the ventilation apertures 37 have a suitable diameter of, for example, about 3 mm to about 5 mm. However, a large diameter may be employed for the apertures for liquid-spotting 36 for supplying a sufficient amount of liquid (10 to 20 $\mu l$ for each electrode surface) to the surfaces of plural pairs of solid electrodes from a set of apertures for liquid spotting. The ventilation apertures 37 may be smaller than the aforesaid diameter and the number of the ventilation apertures 37 may be increased. Furthermore, although a set of apertures for liquid spotting 36 are formed at the center portion of the cover 35 in the embodiment shown in FIG. 3, they may be positioned at another area, i.e., in the area of a set of ventilation apertures 37.

In this embodiment, a construction is employed wherein a twisted thread capillary bridge composed of fibers (hereinafter, the bridge is simply referred to as a thread bridge) is formed on the upper cover 35. However, the thread may be formed on or under the interlayer of the upper cover having a three-layer structure. Also, in an embodiment of this invention, the porous capillary bridge is a twisted thread composed of natural fibers or organic synthetic polymer fibers or filaments such as cotton fibers, silk fibers, polyamide (nylon) fibers, acetate rayon fibers, cured or partially acetalized polyvinyl alcohol fibers, etc. It is preferably comprised of polyamide (nylon) fibers or silk.

Figure 6:
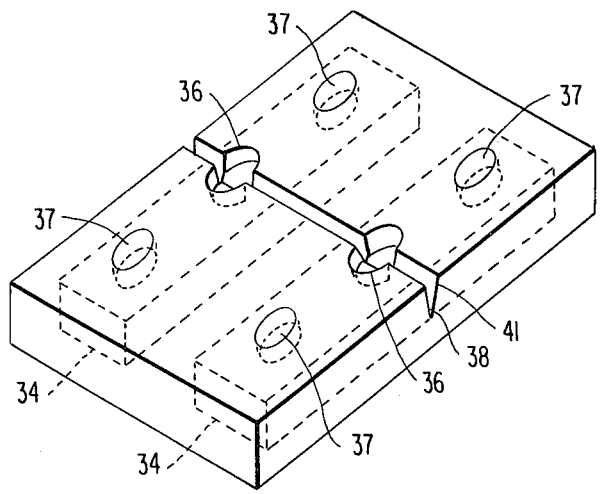
FIG. 6 is a side view showing an embodiment of a part of the device of this invention.

In a preferred embodiment of the foregoing cover 35 and liquid storage member 33, the cover and the liquid storage member are molded in a unitary upper member 40 as shown in FIG. 6. This member 40 shown in FIG. 6 has a set of apertures for liquid spotting 36 and plural ventilation apertures 37 through both surfaces thereof, a V-shaped groove 41 formed on upper surface for connecting the two apertures for liquid spotting 36, and a twisted thread bridge 38 is embeddedd in the V-shaped groove so that the bridge is disposed on the groove, in the inside of the groove, or on the bottom of the groove. The molded member 40 has two liquid storage cells 34 in the inside thereof as decribed above and the foregoing apertures for liquid spotting 36 and ventilation apertures 37 are opened in the liquid storage cells 34. In the liquid storage cells 34 are placed the liquid distribution porous members 32 as described above. The unitary structure of the liquid storage member, the cover, and the thread bridge as described above can simplify the production steps of the device of this invention.

In the foregoing embodiments, a twisted thread bridge composed of fibers is employed as the porous capillary bridge but the porous capillary bridge used in this invention is not limited to such a twisted thread bridge and all the conventionally known porous capillary bridges may be used in this invention. For example, a porous capillary bridge composed of a mixed fiber paper previously proposed by the inventors (Japanese Patent Application (OPI) No. 14050/83, corresponding to GB No. 2,106,253A) can be used in this invention. The use of the twisted thread bridge as described hereinbefore is desirable in that the diffusion of a test solution and a reference solution permeating into the bridge can be limited to one direction and the amount of solutions to be spotted may be reduced. However, the particularly important point of using such a twisted thread bridge is that the bridge can be used for a test solution having a high viscosity, such as whole blood. Furthermore, the employment of a liquid distribution porous member, liquid storage cells, and/or apertures for liquid spotting makes it possible to use a separate bridge or a bridge which is not stuck or fixed onto the surface of the device. That is, if any liquid storage means as described above is or are employed, the electrical conduction of a test solution and a reference solution can be attained by placing a separate bridge on both solutions after spotting the liquids into the apertures for liquid spotting for contacting both liquids therewith. For the porous capillary bridge used in this case, there is a fibrous twisted thread or a filter paper held at the lower edges of a support having a ⊐-shaped sectional form across the space of the support formed between two side walls. Another embodiment of the porous capillary bridge used in this invention is the bridge used for an ionic activity determining device disclosed in Japanese Patent Application No. 69933/82, wherein a lid-form member having a porous capillary bridge is equipped thereto in such a manner that the lid is in an opened state but is closed after spotting liquids for contacting both liquids.

Figure 7:
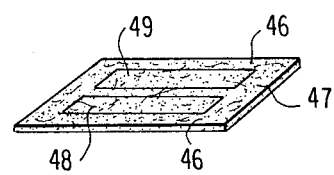
FIG. 7 is a side view showing another embodiment of a part of the device of this invention.

In another embodiment of this invention, a liquid distribution porous member which also acts as a liquid storage member may be employed. It is possible to use a member 47 shown in FIG. 7, which is composed of a sheet of a fibrous material such as that used for the foregoing liquid distribution porous member. This sheet is plugged at the frame portion 46 leaving two liquid storage cell portions 49 unplugged for preventing the liquids stored in the liquid storage cell portions 49 from diffusing into the frame portion 46. Plugging of the foregoing fibrous sheet can be performed by heat welding, by the use of a hot melt type adhesive, by printing using a hardenable hydrophobic ink, etc.

The solid electrodes used in this invention can be prepared by a known method such as disclosed in Japanese Patent Application No. 40398/82. That is, a thin conductive metal layer is formed on a proper electrically insulating support, such as a polymer sheet or film. The thin metal layer can be formed using a vacuum vapor deposition method, electroless plating or chemical plating, etc. A support having a thickness of about 50 μm to about 500 μm, preferably about 80 μm to about 300 μm and having a smooth surface is desirably used. A thickness of the metal layer is about 50 nm to about 50 μm, preferably about 400 nm to about 10 μm. As the metal for the conductive metal layer, a metal having electrical conductivity and stability in the air, such as silver, platinum, palladium, gold, nickel, copper, aluminium, indium, etc., can be used. In order to provide terminals for electrical connection at both end portions of each thin metal layer, masking is applied to the metal layer formed on the support.

Useful masking methods include a method of masking the end portions by coating a known resist, a method of coating the end portions with a liquid resist which can be removed by an alkali as disclosed in *Research Disclosure*, #19445 (June, 1980), a method of masking by forming a thin vapor-deposition layer of nickel or chromium of 5 nm to 20 nm in thickness as disclosed in U.S. Pat. No. 4,259,164, a method of masking by forming a thin vapor-deposition layer of palladium of 1.5 nm to 15 nm in thickness as disclosed in Japanese Patentt Application (OPI) No. 186163/82 or of indium of 3 nm to 20 nm as disclosed in Japanese Patent Application (OPI) No. 33159/83, and a method of masking using a liquid resist having a film-forming property and a peeling-off property after drying, such as a liquid resist composed of polyvinyl chloride as the main component.

After masking the thin metal layer at the terminal portions for electrical connection, the metal layer at the unmasked portion is, if necessary, converted into a water-insoluble salt of the metal or alternatively a water-insoluble salt of the metal may be formed on the thin metal layer at the unmasked portion. When the metal of the thin metal layer is silver, the typical water-insoluble salt of the metal is a halide of the metal, i.e., a silver halide. The metal salt layer is formed by coating or treating the metal layer with a composition containing an oxidizing agent (and a halide ion when the oxidizing agent does not contain a halide ion). The oxidizing agent can be applied to a silver layer by a conventional method such as a roll coating method, a dip coating method, a lamination method, and a brush coating method. The oxidizing agent may be used as a solution thereof in an aqueous solution containing an acid such as hydrochloric acid.

Examples of useful oxidizing agents include $KCrO_3Cl$, $K_3[Fe(3+)(CN)_6]$, $KMnO_4$, $K_2Cr_2O_7$, $NH_4VO_3$, $(NH_4)_2[Ce(4+)(NO_3)_6]$ and $Fe(3+)_2(OOCCOO)_3$. Preferred oxidizing agents are $KCrO_3Cl$, $K_2Cr_2O_7$, and $K_3[Fe(3+)(CN)_6]$. These oxidizing agents may be used solely or in combination. Useful oxidizing agents are described in more detail in, for example, *Handbook of Chemistry and Physics*, 50th Edition, pages D109–114, published by The Chemical Rubber Company, 1969.

The amount of the oxidizing agent used depends upon the thickness of the silver halide layer to be formed but is preferably used in an amount within the range of 0.01 to 2.0 g/m². The silver halide to be formed as a silver halide layer may be silver chloride, silver bromide, or silver iodide. Such a silver halide layer may be also formed by an electrolytic method or other method as disclosed in U.S. Pat. No. 4,214,968. A metal/metal salt (in particular, Ag/AgX, wherein X is a halogen atom) reference electrode can be prepared by using the technique usually used for producing photographic films as disclosed in U.S. Pat. No. 4,214,968, Column 11.

On the metal salt layer thus formed by the method described above can be formed, if necessary, a reference electrolyte layer for the stabilization of electric potential by a known method. The formation of the reference electrolyte layer can be performed using the technique described in, for example, *Research Disclosure*, #16113 (September, 1977), U.S. Pat. No. 4,214,968, and Japanese Patent Application (OPI) No. 17852/82.

An ion-selective layer is a layer capable of selectively responsive to a specific ion and the ion-selective layer can be formed by a known method. For example, an ion-selective layer may be formed by coating a solution prepared by dissolving an ion carrier in an ion-carrier solvent together with a polymer binder in a solvent on the water-insoluble salt layer or the reference electrolyte layer followed by drying by removing a solvent for polymer binder. The concentration of the ion carrier is generally 0.05 to 10 g/m$^2$ and the thickness of the ion-selective layer is about 3 μm to about 125 μm, preferably 5 μm to 50 μm.

The ion-selective layer used in this invention must be water-insoluble since both the test solution and reference solution employed in this invention are aqueous solutions. The ion-selective layer may be either hydrophilic or hydrophobic if the layer is water-insoluble but it is preferred that the layer be hydrophobic.

The meterial constituting the solid electrodes in this invention may be any material generally used for electrodes in this field.

A most typical ion-selective layer is composed of an ion carrier, an ion carrier solvent, and a hydrophobic organic polymer binder (or a matrix composed of a hydrophobic organic polymer binder). Examples of ion carriers include valinomycin, cyclic polyethers, tetralactones, macrolide actins, enniatins, monensin, esters of monensin, gramicidine, nonactin, tetraphenyl borate and cyclic polypeptide.

Examples of ion carrier solvents include trimellitates, bromophenyl phenyl ether, 3-methoxyphenyl phenyl ether, 4-methoxyphenyl phenyl ether, dimethyl phthalate, dibutyl phthalate, dioctyl phthalate, dioctylphenyl phosphate, bis (2-ethylhexyl) phthalate, octyldiphenyl phosphate, tritolyl phosphate and dibutyl sebacate.

Examples of hydrophobic organic polymer binders include hydrophobic natural or synthetic polymers capable of forming films, such as cellulose esters, polyvinyl chloride, polyvinylidene chloride, polyacrylonitrile, polyurethane, polycarbonate and vinyl chloride-vinylidene chloride copolymers.

For the ion carriers, ion carrier solvents, hydrophobic organic polymer binders, solvents for polymer binder and ion-selective layers composed of these materials, the materials and techniques described in, for example, U.S. Pat. Nos. 4,053,381, 4,171,246, 4,214,968 and 4,115,209, and *Research Disclosure*, #16113 (September, 1977) can be used in this invention.

As the material for the ion-selective layer, an ion exchanger may be also used. The ion exchanger used in this invention may be cationic or anionic. Proper ion exchanges and ion-selective layers using these ion exchangers are described in detail in, for example, U.S. Pat. No. 4,115,209.

When the ion to be measured is $K^{30}$, $Na^{30}$, $Ca^{2+}$, $HCO_3^-$, etc., the use of an ion-selective layer is inevitable but when the ion to be measured is $Cl^{31}$, the metal layer of the solid electrodes is composed of silver, and the water-insoluble metal salt layer is composed of silver chloride, the use of an ion-selective layer being unnecessary. In the latter case, a layer composed of the material described in U.S. Pat. Nos. 4,199,411 and 4,199,412, such as a cellulose ester (e.g., cellulose acetate, cellulose acetate butyrate, cellulose acetate propionate, hydrolyzed cellulose acetate butyrate, and mixed esters thereof) or the latex described in, for example, U.S. Pat. Nos. 4,199,362 and 4,256,827 may be formed as an ion-permeable protective layer having permeability with respect to the ion to be measured in place of forming an ion-selective layer. In this invention, such ion-permeable protective layers are include in ion-selective layers.

Each single electrode thus prepared as described above can be used as a pair of two electrodes. It is important for a pair of electrodes to have same electrochemical characteristics. In a preferred embodiment of this invention, a pair of electrodes each having the same properties can be easily constructed by the method proposed in Japanese Patent Application No. 40398/82 by the inventors without requiring the application of a specific insulating means. That is, according to the foregoing method, a single electrode element comprising paired electrodes is prepared by forming functional layers on an insulating support and skiving a groove between each metal layer of the functional layers before, preferably, forming the uppermost ion-selective layer on the functional layers. Skiving can be easily performed using a sharp edged tool such as a knife, etc., the electrical insulation between the separated metal layers (between electrodes) can be completely attained, and further in the electrodes the occurrence of shorting thereof due to the flowing liquid oozed from a bridge, etc., can be prevented by covering the inner edges of the functional layers of the electrodes with a continuous uppermost ion-selective layer.

The electrodes or single electrode elements thus prepared are cut into one electrode or one element. Then, plural pairs of electrodes or plural elements, each pair or element having a different ion-selective layer, are mounted in a support frame, and a water-impermeable adhesive layer, such as double sided adhesive film having punched liquid supplying apertures and ventilation apertures, is stuck to the pairs of electrodes or single electrode elements. A liquid storage member which contains liquid distribution porous members and is then formed in a unitary body with an upper cover is stuck to the surface of the adhesive film to provide the ionic activity determining device of this invention.

Using a device of this invention, ionic activities of different kinds of ions can be simultaneously determined by spotting a test solution and a reference solution each in one operation and measuring an electrical potential difference of each pair. Further, when a thread bridge is used, a test solution having a high viscosity, such as whole blood can be tested with respect to its ion activity.

The invention will now be further described more practically be the following examples.

EXAMPLE 1

On a polyethylene terephthalate film (PET film) of 180 μm in thickness was vapor-deposited a silver layer having a thickness of 500 nm and the film was cut into pieces of 28 mm in width and 1.8 m in length. A groove of 70 μm in depth was formed by skiving the silver metal layer on the PET film at the longitudinal center line using a knife. Both edge portions (3 mm each in width) of the silver layer formed on the film were coated with a solution of a vinyl chloride-vinyl acetate copolymer in a mixed solvent of toluene and methyl ethyl ketone (a film-forming liquid resist for masking capable of being removed by peeling-off after drying) followed by drying to form protective layers each having a thickness of 30 μm. The film was immersed in an oxidative chlorination treatment solution containing 60 mmole/liter of hydrochloric acid and 12 mmole/liter of dichromic acid for 90 sec. at 30° C., washed with water, and dried to provide a solid film-shaped Ag/AgCl reference electrodes.

Then, a solution of 0.9 g of a vinyl chloridevinyl acetate copolymer (VYNS), 1.35 g of methyltrioctyl ammonium chloride, and 0.05 g of didodecyl phthalate dissolved in 5 g of methyl ethyl ketone was coated on the AgCl layer of the foregoing solid film-shaped reference electrodes thus formed in the aforesaid immersion procedure and dried to form a chloride ion-selective layer having a thickness of 25 μm.

Thereafter, the mask layers coated on the edge portions were peeled off to expose the silver metal layer at the terminal portions for electrical connection. The ion-selective solid electrode film was cut into pieces each having a width of 6 mm to provide film-shaped ion-selective electrodes for determining ionic activity of chlorine ion.

EXAMPLE 2

By following the same procedure as in Example 1 using 0.9 g of VYNS, 33 mg of valinomycin, 1.7 g of dioctyl phthalate, and 5 g of methyl ethyl ketone, an ion-selective layer for potassium ion was formed in place of the chloride ion-selective layer in Example 1. The thickness of the potassium ion-selective layer was 30 μm. Then, by the same way as in Example 1, solid film-shaped ion-selective electrodes for determining ionic activity of potassium ion were prepared.

EXAMPLE 3

By following the same procedure as in Example 1 using 0.9 g of VYNS, 0.4 g of methylmonensin, 1.8 g of dioctyl sebacate, and 5 g of methyl ethyl ketone as a coating composition, an ion-selective layer for sodium ion was formed in place of the chlorine ion-selective layer in Example 1. The thickness of the sodium ion-selective layer was 25 μm. In the same manner as in Example 1, solid film-shaped ion-selective electrodes for determining ion activity of sodium ion were prepared.

EXAMPLE 4

By following similar procedures as in Examples 1 to 3, single electrode elements comprising paired ion-selective electrodes, each having a skived silver layer, for ions, $Na^+$, $K^+$, and $Cl^-$ were prepared. On a heat-molded high impact polystyrene support frame 28 of 28 mm in length and 24 mm in width as shown in FIG. 3, were disposed the foregoing three elements (three pairs) each having a width of 6 mm and a length of 28 mm.

A plastic sheet 35 having 2 sets of ventilation apertures 37 and one set of apertures for liquid spotting 36 and a plastic frame or sheet 35 having two liquid storage cells 34 as shown in FIG. 3 were prepared, and both sheets were stuck to each other using a double sided adhesive film to provide an upper cover or upper frame. Then, two medical gauze pieces 32 each having a width of 4.5 mm and a length of 18 mm were inserted in the liquid storage cells 34, respectively, of the cover so that the upper surfaces of the gauze pieces 32 uniformly covered the apertures 36 and 37 of the plastic sheet 33 at the lower side thereof. In this device, one aperture of a set of apertures for liquid spotting 36 was for a reference solution and another aperture thereof was for a test liquid.

Then, a water-impermeable material member 30 composed of a double sided adhesive film having six punched liquid supplying apertures 31 were stuck to the whole lower surface (excluding four coner portions or four marginal portions) of the foregoing upper cover so that the positions of the liquid supplying apertures 31 matched the positions of the apertures for liquid spotting 36 and ventilation apertures 37. Then, a bridge 38 composed of a twisted thread of nylon fibers was disposed on the upper or front surface of the cover and over a set of apertures for liquid spotting 36 and both ends of the bridge were fixed by welding to the surface of the cover by means of a heated soldering iron.

Then, a parting paper at the lower or back side of the double sided adhesive film 30 stuck to the cover was peeled off and the cover with the adhesive tape 30 was stuck to the three single electrode elements 26 placed in the support frame 28. Finally, the cover was fixed to the support frame at the four coner portions or four marginal portions having no adhesive film by heat welding using ultrasonic wave to provide a one-tip type device for determining ionic activities of ions, $Na^+$, $K^+$ and $Cl^-$.

EXAMPLE 5

Using the ionic activity determining device prepared by the method described in Example 4, the potentials based on the ions, $Na^+$, $K^+$ and $Cl^-$ in control serum were measured. Versatol ® was used as a reference solution and Versatol A ® and Versatol AA ® were used as test solutions. The reference solution and the test solution were spotted each once to the central apertures for liquid spotting of the ion activity determining device prepared by the method shown in Example 4 at an amount of 60 μl each. The potential differences after 2 minutes at 25° C. were measured by means of Model 901-type Ion Analyzer, made of Orion K.K. The results obtained are shown in Table 1.

EXAMPLE 6

The same procedure as in Example 5 was followed while spotting once as a test solution 60 μl of whole blood from a rabbit obtained using heparin lithium as an anti-coagulant onto the central aperture for liquid spotting and the potential differences after 2 minutes were measured by the same manner as in Example 5. The results are shown in Table 2-A.

Furthermore, the whole blood of the rabbit was centrifuged to remove erythrocyte and by using the blood plasma as a test solution, the measurement by one spotting was performed as in Example 5. The results obtained are shown in Table 2-B.

TABLE 1

|  | Versatol A | | Versatol AA | |
| --- | --- | --- | --- | --- |
| Measured Ion | Measured Value (mV) | Indicated Value (mEq/l) | Measured Value (mV) | Indicated Value (mEq/l) |
| $Na^+$ | −3.0 | 126 | +1.3 | 151 |
| $K^+$ | +10.8 | 7.3 | −10.2 | 3.1 |
| $Cl^-$ | +2.8 | 91 | −1.5 | 108 |

TABLE 2

| Measured Ion | Measured Value (mEq/l) | |
| --- | --- | --- |
|  | A (whole blood) | B (plasma) |
| $Na^+$ | 145 | 147 |
| $K^+$ | 5.3 | 5.6 |
| $Cl^-$ | 109 | 107 |

EXAMPLE 7

By following the same procedure as in Example 4 using a medical bandage treated with a nonionic surface active agent (an aqueous solution of polyoxyethylene nonylphenyl ether) as the liquid distribution porous member in place of the medical gauze in Example 4, an ionic activity determining device was prepared.

When the same measurement as in Example 5 was performed using the device with respect to ions, Na+, K+, and Cl− in control serum, almost the same results as in Example 5 were obtained.

EXAMPLE 8

By following the same procedure as in Example 4 using Rapia S® (tricot, made by Teijin Limited) in place of the medical gauze, an ionic activity determining device was prepared.

When the same measurement as in Example 5 was performed using the foregoing device with respect to ions, Na+, K+ and Cl− in control serum, almost the same results as in Example 5 were obtained.

While the invention has been described in detail and with reference to specific embodiments thereof, it will be apparent to one skilled in the art that various changes and modifications can be made therein without departing from the spirit and scope thereof.

What is claimed is:

1. In a device for determining ionic activity composed of plural pairs of solid electrodes each pair having an ion-selective layer selectively responsive to a specific predetermined ion as the outermost layer of the solid electrodes and one porous bridge formed thereon for achieving, after supplying a test solution and a reference solution to said pairs of solid electrodes, the electrical conduction between both electrodes in each said pair by the permeation of the solutions through the porous bridge, the improvement comprising said plural pairs of solid electrodes, each electrode pair having one electrode on each of two sides and having a different ion-selective layer, at least one liquid distribution porous member provided for each said side of plural pairs of solid electrodes so that said liquid distribution porous member covers at least partially all the electrodes at each said side, and said bridge disposed on or between said liquid distribution members.

2. The device for determining ionic activity as claimed in claim 1, wherein a water-impermeable material layer having at least a same number of liquid-supplying apertures as the number of said electrodes at the position matching the ion-selective layers of the solid electrodes is formed on the surface of the liquid distribution porous member at the side facing the solid electrodes.

3. The device for determining ionic activity as claimed in claim 2, wherein each of said liquid distribution porous members is placed in the inside of each of two liquid storage cells formed in a liquid storage member each independently disposed on each said side of the plural pairs of electrodes.

4. The device for determining ionic activity as claimed in claim 3, wherein said device further comprises a cover having two apertures for liquid spotting, each aperture for a test solution and a reference solution respectively, and at least two ventilation apertures disposed on said liquid distribution porous members.

5. The device for determining ionic activity as claimed in claim 4, wherein said cover and said liquid storage member are combined into one form.

6. The device for determining ionic activity as claimed in claim 5, wherein said one form is a molded unitary upper member.

7. The device for determining ionic activity as claimed in claim 6, wherein said bridge is disposed on or in said cover extending to or between said apertures for liquid spotting.

8. The device for determining ionic activity as claimed in claim 1, wherein the porous bridge is composed of a twisted thread of fibers and the liquid distribution porous member is composed of fibers.

9. The device for determining ionic activity as claimed in claim 1, wherein each pair of solid electrodes is a single electrode element comprising paired solid ion-selective electrodes comprising a common electrically insulating support having formed thereon a conductive metal layer which is divided into two electrically isolated portions by a groove, a layer of a water-insoluble salt of the foregoing metal, and a common ion-selective layer.

10. The device for determining ionic activity as claimed in claim 1, wherein said device further comprises a lower frame on which said plural pairs of electrodes are mounted.

11. In a device for determining ionic activity composed of plural pairs of solid electrodes each pair having an ion-selective layer selectively responsive to a specific predetermined ion as the outermost layer of the solid electrodes, after supplying a test solution and a reference solution to said pairs of solid electrodes by one porous bridge being brought into contact with said both solutions, achieving the electrical conduction between both electrodes in each said pair by the permeation of both solutions through said porous bridge, the improvement comprising said plural pairs of solid electrodes, each electrode pair having one electrode on each of two sides and having a different ion-selective layer and at least one liquid distribution porous members provided for each said side of plural pairs of solid electrodes so that said liquid distribution porous member covers at least partially all the electrodes at each said side.

12. The device for determining ionic acitivty as claimed in claim 11, wherein a water-impermeable material layer having at least a same number of liquid-supplying apertures as the number of said electrodes at the position matching the ion-selective layers of the solid electrodes is formed on the surface of the liquid distribution porous member at the side facing the solid electrodes.

13. The device for determining ionic activity as claimed in claim 12, wherein each of said liquid distribution porous members is placed in the inside of each of two liquid storage cells formed in a liquid storage member each independently disposed on each said side of the plural pairs of electrodes.

14. The device for determining ionic activity as claimed in claim 13, wherein said device further comprises a cover having two apertures for liquid spotting, each aperture for a test solution and a reference solution respectively, and at least two ventilation apertures disposed on said liquid distribution porous members.

15. The device for determining ionic activity as claimed in claim 14, wherein said cover and said liquid storage member are combined in one form.

16. The device for determining ionic activity as claimed in claim 11, wherein said liquid distribution porous member is composed of fibers.

17. The device for determining ionic activity as claimed in claim 11, wherein each pair of solid electrodes is a single electrode element comprising paired solid ion-selective electrodes comprising a common electrically insulating support having formed thereon a conductive metal layer which is divided into two electrically isolated portions by a groove, a layer of a water-insoluble salt of the foregoing metal, and a common ion-selective layer.

18. The device for determining ionic activity as claimed in claim 11, wherein said porous bridge comprises a twisted thread composed of fibers.

19. The device for determining ionic activity as claimed in claim 11, wherein said device further comprises a lower frame on which said plural pairs of electrodes are mounted.

* * * * *